(12) United States Patent
Schuhbauer et al.

(10) Patent No.: US 11,806,707 B2
(45) Date of Patent: Nov. 7, 2023

(54) METHOD, TUBE BUNDLE REACTOR AND REACTOR SYSTEM FOR CARRYING OUT CATALYTIC GAS PHASE REACTIONS

(71) Applicant: MAN Energy Solutions SE, Augsburg (DE)

(72) Inventors: Christian Schuhbauer, Hunderdorf (DE); Dieter Verbeek, Eging am See (DE); Rolf Bank, Deggendorf (DE)

(73) Assignee: MAN ENERGY SOLUTIONS SE, Augsburg (DE)

( * ) Notice: Subject to any disclaimer, the term of this patent is extended or adjusted under 35 U.S.C. 154(b) by 0 days.

(21) Appl. No.: 15/734,819

(22) PCT Filed: Apr. 24, 2019

(86) PCT No.: PCT/EP2019/060446
§ 371 (c)(1),
(2) Date: Dec. 3, 2020

(87) PCT Pub. No.: WO2019/233673
PCT Pub. Date: Dec. 12, 2019

(65) Prior Publication Data
US 2021/0245129 A1 Aug. 12, 2021

(30) Foreign Application Priority Data
Jun. 8, 2018 (DE) .................. 10 2018 113 735.4

(51) Int. Cl.
*B01J 8/06* (2006.01)
*B01J 8/04* (2006.01)
(Continued)

(52) U.S. Cl.
CPC ............ *B01J 8/067* (2013.01); *B01J 8/0469* (2013.01); *B01J 8/0496* (2013.01); *B01J 8/065* (2013.01);
(Continued)

(58) Field of Classification Search
None
See application file for complete search history.

(56) References Cited

U.S. PATENT DOCUMENTS 3,184,515 A * 5/1965 Penner .................. B01J 8/067
570/245
3,268,299 A 8/1966 Russell
(Continued)

FOREIGN PATENT DOCUMENTS

| CN | 1708350 | 12/2005 |
| CN | 103209760 | 7/2013 |

(Continued)

OTHER PUBLICATIONS

Office Action dated Feb. 9, 2021 issued in India Patent Application No. 202047052909.
(Continued)

*Primary Examiner* — Jennifer A Leung
(74) *Attorney, Agent, or Firm* — Cozen O'Connor

(57) ABSTRACT

A method for carrying out catalytic gas phase reactions including providing a tube bundle reactor which has a bundle of reaction tubes that are filled with a catalyst charge and are cooled by a heat transfer medium, conveying a reaction gas through the catalyst charge, the reaction gas flowing into each reaction tube divided into two part flows introduced in the axial direction of the reaction tube at different points in the catalyst charge the catalyst charge has at least two catalyst layers of different activity, wherein the activity of the first catalyst layer, in the flow direction of the reaction gas, is lower than the activity of the at least one other catalyst layer and in step a first part flow is introduced into the first catalyst layer and each further part flow is introduced past the first catalyst layer into the at least one further catalyst layer.

12 Claims, 7 Drawing Sheets

(51) Int. Cl.
*C07C 1/04* (2006.01)
*C07C 1/12* (2006.01)
*C07C 1/02* (2006.01)
*C07C 9/04* (2006.01)

(52) U.S. Cl.
CPC .............. *C07C 1/041* (2013.01); *C07C 1/042* (2013.01); *C07C 1/048* (2013.01); *C07C 1/12* (2013.01); *B01J 2208/0053* (2013.01); *B01J 2208/00539* (2013.01); *B01J 2208/00548* (2013.01); *B01J 2208/00663* (2013.01); *B01J 2208/065* (2013.01)

(56) References Cited

U.S. PATENT DOCUMENTS

| | | | |
|---|---|---|---|
| 3,970,435 | A | 7/1976 | Schultz et al. |
| 4,342,699 | A | 8/1982 | Palmer et al. |
| 7,449,037 | B2 * | 11/2008 | Lehr .................. B01J 8/065 422/240 |
| 2004/0102530 | A1 * | 5/2004 | Borsa ................. B01J 8/065 422/600 |
| 2005/0002837 | A1 | 1/2005 | Trott et al. |
| 2009/0247653 | A1 | 10/2009 | Ravikumar et al. |
| 2011/0160318 | A1 * | 6/2011 | Bos ..................... B01J 8/06 518/715 |
| 2013/0287652 | A1 | 10/2013 | Lehr et al. |

FOREIGN PATENT DOCUMENTS

| | | |
|---|---|---|
| CN | 103846062 | 6/2014 |
| CN | 105749818 | 7/2016 |
| CN | 106132529 | 11/2016 |
| DE | 1645840 | 7/1970 |
| DE | 2549439 | 5/1976 |
| DE | 2705141 | 8/1978 |
| DE | 3006894 | 9/1980 |
| DE | 2940334 | 4/1981 |
| DE | 19723322 | 12/1998 |
| DE | 102009059310 | 6/2011 |
| DE | 102010040757 | 3/2012 |
| EP | 2110425 | 10/2009 |
| EP | 3068754 B1 | 1/2018 |
| GB | 472629 | 9/1937 |
| JP | S 34-009859 B | 11/1959 |
| JP | S 55-113730 | 9/1980 |
| JP | S 59-133293 | 7/1984 |
| JP | S 61-061632 | 3/1986 |
| JP | 2003-321400 | 11/2003 |
| JP | 2013-136538 | 7/2013 |
| WO | WO 2012035173 | 3/2012 |
| WO | WO 2015/067656 | 5/2015 |
| WO | WO 2015150420 | 10/2015 |

OTHER PUBLICATIONS

Office Action dated Aug. 27, 2021 issued in Chinese Patent Application No. 201980038267.0.
Office Action dated Feb. 28, 2022 issued in Japanese Patent Application No. 2020-568315.
Search Report dated Feb. 4, 2019 issued in German Patent Application No. 10 2018 113 735.4.
Reschetilowski V.: Introduction to Heterogeneous Catalysis, Springer Verlag Berlin Heidelberg 2015, p. 11-20, DOI 10.1007/978-3-662-46984-2_2.
Office Action dated Aug. 1, 2022 issued in Korean Patent Application No. 10-2021-7000652.
Office Action dated May 24, 2023 issued in European Patent Application No. 19719844.3.

* cited by examiner

METHOD, TUBE BUNDLE REACTOR AND REACTOR SYSTEM FOR CARRYING OUT CATALYTIC GAS PHASE REACTIONS

CROSS REFERENCE TO RELATED APPLICATIONS

This is a U.S. national stage of Application No. PCT/EP2019/060446 filed Apr. 24, 2019. Priority is claimed on German Application No. DE 10 2018 113 735.4 filed Jun. 8, 2018 the content of which is incorporated herein by reference.

BACKGROUND OF THE INVENTION

1. Field of the Invention

The invention relates to a method and a tube bundle reactor for carrying out catalytic gas-phase reactions and to a reactor system for carrying out catalytic gas-phase reactions. In particular, the invention relates to the carrying out of exothermic catalytic gas-phase reactions with distinct temperature maxima. An example for such reactions are methanation reactions.

2. Description of Related Art

Against the background of finite natural gas deposits, there is increasing interest in the production of a natural gas substitute. This gas designated as "SNG"—"substitute natural gas" or "synthetic natural gas"- or "replacement gas" substantially contains methane and small fractions of non-reacted and other gases that must comply with the feed-in specification of the respective gas network if the SNG is to be fed in there.

SNG can be produced on the basis of coal or other carbon-containing substances such as waste or biomass by synthesis gas—a mixture of CO and/or $CO_2$, $H_2$, and possibly other components such as water. In another method methanation is used for the chemical storage of, for example, excess power which occurs when producing electrical power by renewable energies. Hydrogen is produced by electrolysis using this current. Carbon dioxide is preferably obtained from waste gases of industrial processes or from biogas plants. In this case, the feed gas for the methanation consists almost exclusively of $CO_2$ and $H_2$.

The methanation is crucially determined by the following chemical reactions:
CO Methanation:

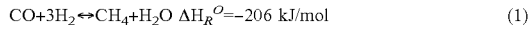

$$CO + 3H_2 \leftrightarrow CH_4 + H_2O \quad \Delta H_R^O = -206 \text{ kJ/mol} \quad (1)$$

$CO_2$ Methanation ("Sabatier Reaction")

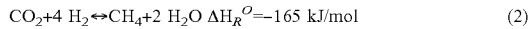

$$CO_2 + 4H_2 \leftrightarrow CH_4 + 2H_2O \quad \Delta H_R^O = -165 \text{ kJ/mol} \quad (2)$$

Hydrogen-Shift Reaction ("WGS Reaction")

$$CO + H_2O \leftrightarrow H_2CO_2 \quad \Delta H_R^O = -41 \text{ kJ/mol} \quad (3)$$

In addition, a plurality of other side reactions also take place, including the Boudouard reaction in which carbon monoxide decomposes to give carbon and carbon dioxide.
Boudouard Reaction:

$$2\,CO \leftrightarrow C + CO_2 \quad \Delta H_R^O = -173 \text{ kJ/mol} \quad (4)$$

The reactions are usually catalyzed with elements of the VIII subgroup, preferably with nickel.

All the reactions are in equilibrium with one another wherein the position of the equilibria can be varied by suitable measures. For the position of the equilibrium the dependences of the essential process parameters—pressure, temperature, and concentrations of the reaction components—are obtained from the reaction equations:

In Equations (1) and (2) a reduction in volume is obtained on the product side. Both reactions are additionally highly exothermic. This has the result that a high pressure and a low temperature shift the reaction equilibrium to the product side. With increasing pressure however, its influence on the reaction equilibrium becomes increasingly less. In addition, the wall thicknesses of all the pressurized apparatus parts become increasingly greater and requirements for the tightness increase, intensified by the small molecular size of hydrogen.

The reaction temperature has a lower limit due to the minimum operating temperature of the catalyst. An increasing reaction temperature certainly increases the reaction rate and reduces the size of the reaction apparatus accordingly. A disadvantage however is a limitation of the conversion as a result of a shift of the reaction equilibrium to the educt side and an increased ageing of the catalyst.

The reaction equilibrium can be further shifted to the product side by removing the process component water $H_2O$ from the reaction system. However, this promotes the formation of soot by the Boudouard reaction according to Equation (4). This reaction is suppressed by a minimum content of water. A feed gas having an almost stoichiometric composition is favourable, otherwise the over stoichiometric component is left over. This is not a problem as long as this component lies within the specification of the feed-in gas. Otherwise, a separation is required, which leads to increased costs.

In heterogeneously catalyzed exothermic gas-phase reactions, a reaction zone having particularly strong heat generation is frequently formed in the initial region of the catalyst charge, with the result that a more or less distinct temperature profile having a maximum in this reaction zone is formed in the catalyst charge in the flow direction. The region of the temperature maximum is also designated as "hot spot". This temperature maximum is desired per se as long as it does not exceed a certain limit. The high reaction temperature results in a high reaction rate with the result that the length of the catalyst charge is reduced as far as the reaction equilibrium. However, in exothermic equilibrium reactions at high temperature the conversion decreases. In order to increase the conversion, the temperature of the reaction gas must then be reduced.

Especially in methanation reactions this hot spot is very distinct. If it is not adequately controlled, this can result in an excessive increase in temperature with the consequence of an increased ageing of the catalyst and associated reduction in conversion. This necessitates more frequent costly exchange of the catalyst. In addition, there is the risk of damage to thermometers if these are built into individual reaction tubes.

An attempt was made to take account of these reaction-technical boundary conditions using various methods, tube bundle reactors and reactor systems.

The gases participating in the chemical reactions are hereinafter designated as "feed gas" as long as they are located just before the entrance into a tube bundle reactor or into a reactor system. From entrance into a tube bundle reactor or into a reactor system, the gases are designated as "reaction gas", from completion of the chemical reactions they are designated as "product gas".

In order to control the temperature of exothermic catalytic gas-phase reactions in a tube bundle reactor with catalyst-filled reaction tubes, GB472629 proposes to vary one or more of the reaction conditions—surface area, thickness or activity of the catalyst, gas speed, turbulence or flow cross-section—continuously or in a stepped manner. Thus, for example, in regions with strong heat generation, a correspondingly strong reduction in the flow cross-section is required which in turn results in correspondingly high pressure losses. Such pressure losses make more powerful condensers necessary and thus result in increased investment and operating costs.

In another procedure for controlling the hot spot in a tube bundle reaction it is proposed in U.S. Pat. No. 3,268,299 to embed a metering tube in the catalyst charge in each reaction tube and introduce the reaction gas into the metering tube. The metering tube extends from the gas-inlet-side end of the reaction tube into the catalyst filling, is free from catalyst material and has a plurality of axially distributed outflow openings which all open into the catalyst charge. As a result, the reaction is distributed over the length of the reaction tube, with the result that the reaction intensity is reduced and the temperature increase is reduced. On the other hand, the metering tube brings about a reduction in the hydraulic diameter of the catalyst charge and therefore a reduction of the radial transport path for the reaction heat and therefore more rapid removal thereof. In another design, a reaction gas component A can be guided into the metering tube and a reaction gas component B can be guided into the beginning of the catalyst charge.

DE 102010040757A1 proposes a tube bundle reactor whose catalyst-filled reaction tubes provided with metering tubes extend through two heat transfer medium zones, wherein the outflow openings of the metering tubes all open inside the first heat transfer medium zone into the catalyst charge. The reaction gas in each reaction tube is guided simultaneously both into the inlet of the catalyst charge and also into the metering tube. This construction specifically enables an optimal reaction control due to the stepped reaction gas supply and an optimal temperature control due to independent heat transfer medium cycles but it is very expensive if only a small amount of heat is generated in the second heat transfer medium zone.

A widely used method for methanation are reactor systems with at least two reactor stages, wherein the first reactor stage is a high-temperature methanation in which high reaction rates are achieved at high temperature. In a second reactor stage in a low-temperature methanation the reaction is continued as far as the desired conversion.

Frequently a plurality of adiabatic catalytic fixed-bed reactors with interposed cooling stages are connected in series. If the feed gas is supplied completely to the first reactor, this is frequently diluted with cycle gas from downstream reaction stages in order to avoid too-high reaction temperatures. Before entry into the reactor the feed gas is temperature-controlled with a pre-heater to the minimum operating temperature of the catalyst. A corresponding method is presented in DE2549439A. In a method presented in EP2110425A1 the feed gas is divided up and supplied in parallel to the entrance of a plurality of adiabatic fixed-bed reactors connected in series. The feed gas can be additionally diluted by addition of water vapour. The process is operated, for example, at about 35 bar, the inlet temperature in the reactor lies between 240° C. and 300° C., the outlet temperature is about 600° C. The reaction heats are used process-internally for temperature control of the gas and in other parts of the installation.

It was also proposed to embed coiled tubes in consecutively connected reactors in the catalyst charge of one of these reactors in order to cool the reaction gas more effectively. Such isothermal methanation reactors with boiling water cooling combined with adiabatic reactors are described in DE2705141A1 or in DE2940334A1. In the last publication the process is operated with excess hydrogen. The non-converted hydrogen is removed from the product gas and returned to the feed gas.

DE 1645840A proposes a two-stage methanation process in which after the first methanation stage so much water vapour is removed from the reaction gas that precipitation of carbon on the catalyst is prevented. In US2009/0247653A1 such a partial condensation is carried out after the reaction gas has flowed through two methanation reactors. In DE102009059310A1, in two consecutively connected reactors with external cooling, such partial condensation is carried out between these two reactors.

SUMMARY OF THE INVENTION

It is the object of one aspect of the invention to improve a method, a tube bundle reactor, and a reactor system of the type mentioned initially so that catalytic gas-phase reactions with distinct temperature maxima can be carried out more safely, more rapidly and in this case with small installation size and that at the same time the lifetime of the catalyst is increased.

The concept of catalyst activity is familiar to the person skilled in the art and is described in detail, for example, in the article "Reschetilowski W.: Introduction to Heterogeneous Catalysis, Springer Verlag Berlin Heidelberg 2015, p. 11-20, DOI 10.1007/978-3-662-46984-2_2.

As a result of the measures according to one aspect of the invention, the effectiveness of catalytic gas-phase reactions is improved appreciably with increased operating safety since a more precise control or guidance of the reaction temperature is achieved and a higher throughput is obtained. The measures according to the invention are based on the finding that in a tube bundle reactor in which a metering tube is embedded in the catalyst charge of the reactor tubes, the interior of which is catalyst-free, not only the radial heat transfer path is shortened there but the flow cross-section of the catalyst charge in the flow direction of the reaction gas is reduced and in this reduced flow cross-section reaction gas is introduced into the catalyst charge as partial flows at axially different points with the result that the heat loading of the catalyst charge is equalized and thus the temperature maximum is reduced. An additional finding is that the reaction gas flowing out from the gas outflow points of the metering tube—i.e. the corresponding partial flows—is diluted by the reaction gas already flowing in the catalyst charge and reacted upstream. Instead of a particularly strongly defined temperature maximum in the initial region of the catalyst charge, a plurality of smaller temperature maxima therefore occur in the flow direction of the reaction gas. Consequently, the amount of reaction gas entering into the catalyst charge is certainly reduced locally by the partial flows and the released reaction heat is controlled and the reaction gas partial flows entering into the catalyst charge downstream are also diluted by the reaction gas already flowing in the catalyst charge and reacted upstream but in the partial flow which enters directly into the catalyst charge above the first downstream partial flow such a reaction-controlling effect does not occur. Here it is the case that the undiluted reaction gas reacts under the influence of an undiluted catalyst even after a short inlet section and forms a defined hot spot. This hot spot can be controlled up to a certain degree by a corresponding dimensioning of the annular gap between metering tube and reaction tube.

As the annular gap becomes smaller, the radial distance to the cooled reaction tube wall is initially reduced. However, the reduced flow cross-section results in a smaller hydraulic diameter and therefore in a greater pressure loss. In order to maintain a constant flow rate, the initial pressure must be increased and the gas flow in the metering tube must be throttled. The consequence is increased investment costs and operating costs for the compressor. Since the catalyst volume in the annular space is reduced, the reaction tube must be lengthened accordingly in order to arrive at the equilibrium state. Alternatively it is possible to increase the number of reaction tubes. In each case, the ratio of the hydraulic diameter of the annular gap to the particle size of the catalyst is smaller with the consequence of an increased wall effect and correspondingly undefined reaction conditions.

The disadvantages of a more powerful compressor and an excessive increase in the catalyst volume are now avoided since according to the invention the activity of the first catalyst layer is reduced. Since the chemical reactions according to the requirements take place under the action of catalysts, the conversion therefore initially decreases. However, this is opposed by several influences which result in an increase in the conversion and therefore approximately cancel out the conversion-reducing effect of the reduced catalyst activity. As a result of the reduced catalyst activity, firstly less reaction heat is produced which results in a reduction in the level of the temperature of the hot spot. A reduced gas temperature now reduces the volume flow and therefore the pressure loss which is dependent on the gas velocity, which in turn results in an increased mass flow through the first catalyst layer. An equilibrium with respect to the parallel gas flow inside the metering tube is established. As already described initially, at the same time the conversion now increases with the decreasing temperature. The increase in the gas fraction in the first catalyst layer furthermore has the result that the reaction gas entering into the catalyst from the first gas outlet point from the metering tube undergoes an increased dilution with the result that the subsequent hot spot is controlled more effectively. The same applies to the following gas outlet points or reaction sections. Overall the conversion at the end of the reaction tube therefore remains substantially constant. In this way, the temperature control in the initial region of the catalyst charge is significantly improved, wherein the conversion, the flow cross-section and the pressure loss remain substantially unchanged. The crucial advantage of the measure according to the invention lies in that due to the improved control of the temperature of the hot spot in the first catalyst layer, the lifetime of the catalyst is significantly increased. Thus, with the same interval for replacing the catalyst, the reactor according to the invention has a significantly higher catalyst activity than a reactor with undiluted catalyst designed according to the prior art so that more product can be produced in a given production time interval.

The degree of conversion achieved with a tube bundle reactor according to one aspect of the invention is already sufficient for specific purposes. Thus, in the case of a methanation reaction the product gas with the methane concentration achieved can be used to feed into an L gas network or for combustion in combined heat and power plants.

By replacing the catalyst material of the first catalyst layer, the reaction conditions can be adapted relatively easily to different requirements and in particular to changing conditions in the tube bundle reactor. Thus, a particularly effective temperature control is possible at any time. Thus, a controlled hot spot damped according to a specification is formed in the first region of the catalyst layer. This then fades away and the temperature in the catalyst layer changes only slightly. This last region of the small temperature change preferably accounts for a fraction of 10 to 40% of the first catalyst layer.

A further advantage of the method according to the invention lies in that there is no need to return product partial flows for cooling or dilution.

The method is suitable for all heterogeneously catalyzed exothermic gas-phase reactions which form a hot spot in the initial region of the catalyst charge. The invention is particularly suitable for those reactions in which this hot spot is particularly strongly defined and accordingly is difficult to control.

Preferably the catalytic gas-phase reaction includes methanation reactions as an example for such reactions. For the methanation reaction according to Equation (2), the feed gas for carrying out the method according to the invention preferably consists of $CO_2$ and $H_2$. When using $CO_2$ and $H_2$ as components of the feed gas in stoichiometric composition, after separation of water at the end of the process, a product gas having a composition according to the equilibrium conditions at given pressure and temperature can be expected. In fact, the methane content is somewhat lower, possibly because the educt gas is not present precisely in stoichiometric composition. In the case of a non-stoichiometric feed gas composition, one or other component is always left over after the reaction. The choice of the feed gas composition is determined according to the respective feed conditions for the SNG. Thus, for example, the hydrogen $H_2$ should be converted as completely as possible so that the process is preferably carried out in a range between stoichiometric composition of $CO_2/H_2$ and a slight excess of $CO_2$. The preferred range of the ratio of $CO_2/H_2$ in this case lies between 0.25:1 and 0.26:1.

In this case, the activity of the first catalyst layer is preferably set to 5% to 90% and particularly preferably to 10% to 40% of the activity of the at least one further catalyst layer. As a result of this measure, the temperature level of the hot spot is damped in a safe and defined manner, with the result that the conversion remains at a high level and the lifetime of the catalyst is lengthened. If temperature measurement devices are installed in reaction tubes, these are protected from damage. As a result, a safe and permanent process monitoring is ensured.

According to one aspect of the invention, the first and second catalyst charge can each be subdivided into further catalyst layers having different catalyst activities, wherein preferably the catalyst activity increases from catalyst layer to catalyst layer.

According to one aspect of the invention, the reaction parameters in the tube bundle reactor, in particular the heat transfer medium temperature, the charge heights of the individual catalyst layers, the axial spacings of introduction points of the partial flows, the partial flow quantities and the catalyst activation are set so that the maximum temperatures in the first and second catalyst layer lie in a range from 300° C. to 900° C., preferably from 500° C. to 700° C. The controlled high temperatures inside the catalyst charge result in an optimum with regard to reaction rates and conversion. As a result, the tube bundle reactor only requires a relatively small reaction space. As a result of the stepped arrangement of the introduction points in the tube bundle reactor combined with catalyst layers of different activity, both a particularly high reaction rate with correspondingly small reaction volume is achieved and also a particularly high conversion in the range of lower temperatures. In this way, the necessary entire catalyst volume can be further minimized.

Preferably the reaction heats generated in the process are used process-internally and particularly preferably also apparatus-internally.

Due to the temperature ranges, several types of heat transfer medium come into question. Boiling water is preferred. However, in a tube bundle reactor having a jacket diameter in the range of 5 to 8 metres, the wall thicknesses at corresponding pressure become so great that the tube bundle reactor can no longer be constructed economically. Thus, in some cases cooling using a heat transfer medium which is liquid under operating conditions can be more favourable. Here pressureless operation, for example, using liquid salt, ionic liquids or a heat transfer medium oil can be used.

Usually all the heat-resistant steels customary in the building of pressure vessels such as, for example, the material having the abbreviation 16Mo3 or similar materials come into consideration as materials for the tube bundle reactor. Depending on the place of usage and the type of stressing, other materials can also be used.

For controlling the temperature, individual reaction tubes are fitted with thermometers which allow a temperature measurement along the reaction tubes.

Preferably the reaction gas is introduced into the tube bundle reactor at a pressure of 5 bara to 50 bara and preferably of 10 bara to 30 bara and particularly preferably from 15 bara to 25 bara. This pressure range is optimal with regard to the influencing of the reaction equilibrium taking into account the constructive expenditure which primarily consists in the strength design and the investment and operating costs for compressing the feed gas at the entrance to the tube bundle reactor.

Preferably the heat transfer medium temperature of the tube bundle reactor is set so that it lies in the range of 240° C. to 300° C. This temperature range is optimal with regard to the influencing of the reactions with regard to reaction rate and conversion. In some cases, the method according to the invention can also be carried out at temperatures in the range between 200° C. and 350° C. The start-up temperature of the catalyst which must not be fallen below is crucial for the lower temperature limit.

In a favourable aspect of the invention, the tube bundle reactor forms a first reaction stage of a reactor system which further comprises a condenser, a heating zone and a second reaction stage, which are all arranged consecutively in the flow direction of a reaction gas flowing through the reactor system, wherein step b) is followed by the further steps:
  c) cooling the reaction gas flowing out of the tube bundle reactor to a temperature below the dew point of at least one portion of the components of the reaction gas and diverting at least a portion of the condensed components;
  d) heating the reaction gas from which a portion of the condensed components was diverted in step c);
  e) providing a reactor with a second catalyst charge as a second reaction stage; and
  f) guiding the heated reaction gas through the second catalyst charge.

In these measures the basic idea is to optimize respectively one parameter in each individual reactor stage. The aim of the first reactor stage is a controlled high reaction rate. By this means the reactor dimensions are additionally minimized and the lifetime of the catalyst is lengthened. In the second reactor stage the residual conversion takes place at low temperature. In this residual conversion only a little reaction heat is generated. In order to fulfil this function, the constructive configuration of the second reactor stage can be simplified appreciably and usually a simple adiabatic catalytic fixed-bed reactor is sufficient.

The conversion of the educts at the end of the first reactor stage lies in the range of 90% to 99%. The residual conversion takes place in the second reactor stage. The conversion in the first reactor stage is limited by the reaction product water as a result of the equilibrium reaction. Due to the partial condensation after the first reactor stage, water is taken from the reaction system so that the reaction equilibrium is shifted further to the product side. Due to the high conversion of the first reactor stage, the reaction heat in the second reactor stage is so low that here a simple adiabatic fixed-bed reactor is usually sufficient for the residual methanation.

Preferably the reaction gas is guided through precisely two reactor stages. As already mentioned above, the reaction parameters can be set so that the residual conversion of the educts takes place in the second reactor stage and thus the total conversion of the educts is completed and a further reactor stage is no longer required. In particular in methanation reactions this means that after the second reactor stage, after condensing out the water fraction the product gas meets the feed-in specification of the respective gas network into which it is to be fed.

When designing the second reactor stage in the case of methanation, the main aim is to achieve a methane concentration corresponding to the feed-in specification. This is achieved by a high conversion at relatively low temperature. The lower temperature limit is determined by the minimum operating temperature of the catalyst, also designated as "start-up temperature". The upper temperature limit is determined by the temperature resistance of the catalyst and the conversion to be maintained. A high pressure also has a favourable effect.

All known solid catalysts and shell catalysts for methanation come into consideration as material for the catalyst. These usually contain elements of the VIII side group, preferably nickel.

In a favourable further development of the invention, in step c) the reaction gas is cooled to a temperature below the dew point of water and at least a portion of the condensed water is diverted. As a result of the partial condensation and diversion of the reaction product water between the first reactor stage and the second reactor stage, the reaction equilibrium is shifted to the product side in a favourable manner.

In this case, after diverting at least a portion of the condensed water, the reaction gas advantageously contains a residual water vapour content of 0% to 30% and preferably of 15% to 25%. As a result of the reaction gas containing a residual quantity of water vapour, soot formation is prevented and the process is therefore stabilized. Before entering into the second reactor stage, the reaction gas similarly to the feed gas is heated in a pre-heater to somewhat above the start-up temperature. With this residual water vapour content, an optimum is achieved with regard to the shift of the reaction equilibrium onto the product side and the avoidance of soot deposits.

Preferably the entire reactor system is operated at a space velocity (GHSV) of 5000 l/h to 20000 l/h, preferably of 8000 l/h to 15000 l/h. Here the space velocity "GHSV" means the "gas hourly space velocity". This is the standard volume flow related to the bulk volume of the entire catalyst contained in the reactor system, wherein here the bulk volume relates to catalyst charges of any type—whether undiluted or diluted. A high space velocity with the same reactor power results in a smaller reactor volume. This results in reduced investment costs and constructive advantages due to a reduced space requirement.

The reduction of the catalyst activity in a tube bundle reactor according to the invention is preferably achieved by diluting a catalyst with an inert material. The dilution ratio of catalyst to inert material preferably lies in a range of 1:1 to 1:10 and particularly preferably in a range of 1:2.5 to 1:4. The ratios relate to the bulk volumes of the individual components.

By diluting the catalyst with inert particles to achieve a specific activity, one is very flexible in the choice of a suitable catalyst.

If a change of catalyst should be necessary, this will frequently only be restricted to the range having the highest reaction temperatures, i.e. to the region with the diluted catalyst. Here the probability of damage is the highest.

The degree of dilution of the first catalyst layer with the aim of a reduced catalyst activity depends in this case in particular on the basic activity of the undiluted catalyst, on the flow rate, the GHSV and on the inlet temperature.

The shape of the particles which can be used for the catalyst is not particularly limited. In principle, all known mouldings can be used, thus, for example, spheres, pellets, saddles, or cylinder rings. The particles should have a good flow behaviour and should not settle after pouring in, i.e. the height of the charge should ideally not change during operation. They should be conditioned so that the flow behaviour in the annular space between reaction tube inner wall and metering tube outer wall differs only slightly from the flow behaviour of a particle charge having a large flow area. The flow behaviour means in particular the pressure loss and the wall effect.

Particularly preferred are cylinder pieces having a diameter in the range of 1.2 mm to 3.0 mm, a length in the range of 3.0 mm to 8.0 mm and a length/diameter ratio in the range of 1:1 to 8:1. In this embodiment the particles for use as solid catalyst are preferred.

The size and shape of the catalyst particles and inert particles are usually approximately the same. As a result, a demixing of the two types of particles is prevented.

According to one aspect of the invention, catalyst particles and inert particles are different in size and/or in shape. This configuration can be particularly advantageous if, for example, inert particles of the same type as catalyst particles are difficult to procure or inert particles of a different type are significantly more economical. Combinations of different features can also be given by which properties such as pressure loss, heat conduction or heat transfer can be specifically optimized. The individual parameters of this configuration cannot be specified in advance. They must be investigated and specified separately in individual cases.

In the case of deviations of shape and size of the two types of particles with respect to one another, a filling method is preferably used which is particularly aligned to prevent demixings.

Preferably in the tube bundle reactor according to one aspect of the invention, the fraction of the first catalyst layer to the (first) catalyst charge is 5 vol. % and 50 vol. %.

The fraction of the first catalyst layer with reduced activity to the total catalyst volume is the result of the process simulation. Usually a fraction in a range of 10 vol. % to 35 vol. % of the total catalyst volume of the (first) catalyst charge is obtained. In the first catalyst layer and in the initial region of the second catalyst layer a rapid conversion is achieved at high temperature. The subsequent hot spots following each further gas outflow point are preferably more weakly defined in their height.

Preferably flow takes place from bottom to top in the tube bundle reactor, i.e. flow takes place from bottom to top in the reaction tubes. Accordingly, the metering tube of one reaction tube is fastened at the lower end and ends inside the catalyst charge. As a result of this arrangement, the pouring of the catalyst into the reaction tubes is highly simplified since the upper ends of the reaction tubes are free from installations in this arrangement.

When using the tube bundle reactor according to one aspect of the invention for methanation reactions, reaction tubes having an external diameter in the range of 20 mm to 100 mm, preferably in the range of 20 mm to 40 mm have proved particularly successful with wall thicknesses in the range of 1.5 mm to 3.0 mm. The metering tube preferably has an external diameter in a range of 6 mm to 85 mm, particularly preferably of 6 mm to 15 mm, with a wall thickness in the range of 1.0 mm to 2.0 mm.

The cross-sectional shape of the metering tubes is arbitrary. The cross-section can, for example, be circular or oval or even quadrilateral. A plurality of parallel metering tubes in one reaction tube are also possible.

Preferably the at least two catalyst layers contain the same catalyst material and the first catalyst layer contains 5 vol. % to 90 vol. %, preferably 10 to 40 vol. % of the catalyst material of the at least one further catalyst layer. In this way, only a single type of catalyst needs to be procured. With this one type of catalyst, the catalyst activity of the first catalyst layer can be flexibly set by diluting with inert material. In practice, a process optimization is initially carried out by numerical simulation. As a result, a first, optionally still relatively wide optimal range of the degree of dilution is obtained. A further optimization can be achieved by technical tests. Here the first already-determined range is examined and optionally further optimized, i.e., specified more accurately.

In an advantageous embodiment of the invention, in each reaction tube the ratio of the annular gap between the inner wall of the reaction tube and the outer wall of the metering tube to the particle diameter of the first catalyst layer lies in the range of 2 to 6. This ratio is particularly advantageous with regard to handling ability, heat transfer and catalytic efficiency.

Preferably the axial spacing between the at least one gas inflow point and the first gas outflow point in the flow direction of the reaction gas, the axial spacing between the gas outflow points and the axial spacing between the last gas outflow point and the end of the metering tube and the number thereof are selected so that a heating surface loading due to the reaction heat released between the gas inflow or outflow points is in the range of 10 kW/m$^2$ to 150 kW/m$^2$, preferably in the range of 20 kW/m$^2$ to 50 kW/m$^2$. The reference surface here is the tube outer surface. With this boundary condition with regard to the heat production, a favourable ratio with respect to the heat removal is achieved which in turn results in advantageous reaction temperatures.

In a favourable further development of the invention, the square ratio of the internal diameter of the reaction tube to the external diameter of the metering tube lies in a range of 2 to 6. With these preferred ratios, an annular gap is obtained which particularly meets the requirements for a reaction control.

The reactor system according to one aspect of the invention has a plurality of components which influence one another. Preferably the individual components are designed with the aid of a simulation program. Such a simulation program can be a commercially available program or a program which can be self-created using known process-technology relationships. The catalysts have different activities depending on the composition. The parameters of the catalyst used are determined for this purpose in laboratory tests and the simulation parameters are thus adapted. The sizes of the first and second reactor stages influence one another. The larger the first reactor stage, i.e. the more catalyst volume is present there, the greater is the conversion there. The second reactor stage is correspondingly smaller. Conversely it holds that a smaller first reactor stage requires a larger second reactor stage. In optimization calculations the reactor system can be optimized, for example, to a minimum total quantity of catalyst under given boundary conditions with respect to mass throughput and methane concentration.

If the conversion of the first reaction stage is too low, a critical operating case can occur in the second reactor stage in which so much reaction heat is released locally so that the temperature rises so steeply that firstly the catalyst is damaged and secondly the conversion drops below a specific value which normally corresponds to at least that of the feed-in specification. There is additionally the risk of damage to the reaction apparatus. In order to create a reserve for the case where the catalyst activity of the first reactor stage decreases in the course of the operating time, the second reaction stage is therefore preferably dimensioned so that even in the event of a decrease of the conversion in the first reaction stage to a worst predictable value, the limiting conversion in the second reaction stage which results in a critical operating case is not reached. Preferably an adiabatic catalytic fixed-bed reactor is used for the second reactor stage. Its simple construction increases the economic viability of the reactor system.

Preferably at least two of the units first reactor stage, condenser, heating zone and second reactor stage form a constructive unit. If first and second reactor stage are arranged in a reactor housing, the two reactor stages can either be arranged sequentially or parallel. The combining of individual units in a constructive unit results in a compact production system. More compact constructive units increase the clarity of the system and result in cost savings. In cases of apparatus-internal heat usage, heat losses are minimized. In some cases, the second reactor stage is also designed as an isothermal catalytic reactor. This can be advantageous if both reaction stages are arranged in one reactor housing.

In a favourable aspect of the invention, the second reactor stage is a cooled reactor whose average heat transfer medium temperature is 0 K to 30 K lower than the heat transfer temperature of the first reactor stage. This temperature range is optimal in relation to reaction rate, attainable conversion and overall size of the individual units of the reactor system.

In this case, the second reactor stage is preferably a tube bundle reactor having a bundle of reaction tubes which are filled with the second catalyst charge and through which a reaction gas flows during operation and which are cooled by a heat transfer medium. This variant increases the flexibility of the overall system since it is possible to reduce the conversion of the first reactor stage and accordingly increase the reaction heat in the second reactor stage. This procedure can be appropriate if, for example, two identical reactors present an alternative to two different reactors for constructive or economic reasons or offer joint heat usages.

Particularly preferably the reaction tubes of the two reactors are located in a common heat transfer medium space. With the arrangement of the two reactor stages in a common heat transfer medium space, one reaction apparatus is saved. The reactions of the two reactor stages can be controlled simultaneously. As a result of the metering tubes in the first reactor stage, very different adapted reaction conditions can nevertheless be set.

BRIEF DESCRIPTION OF THE DRAWINGS

The invention will be explained in detail hereinafter with reference to the drawings as an example. In the figures.

DETAILED DESCRIPTION OF THE PRESENTLY PREFERRED EMBODIMENTS

Figure 1:
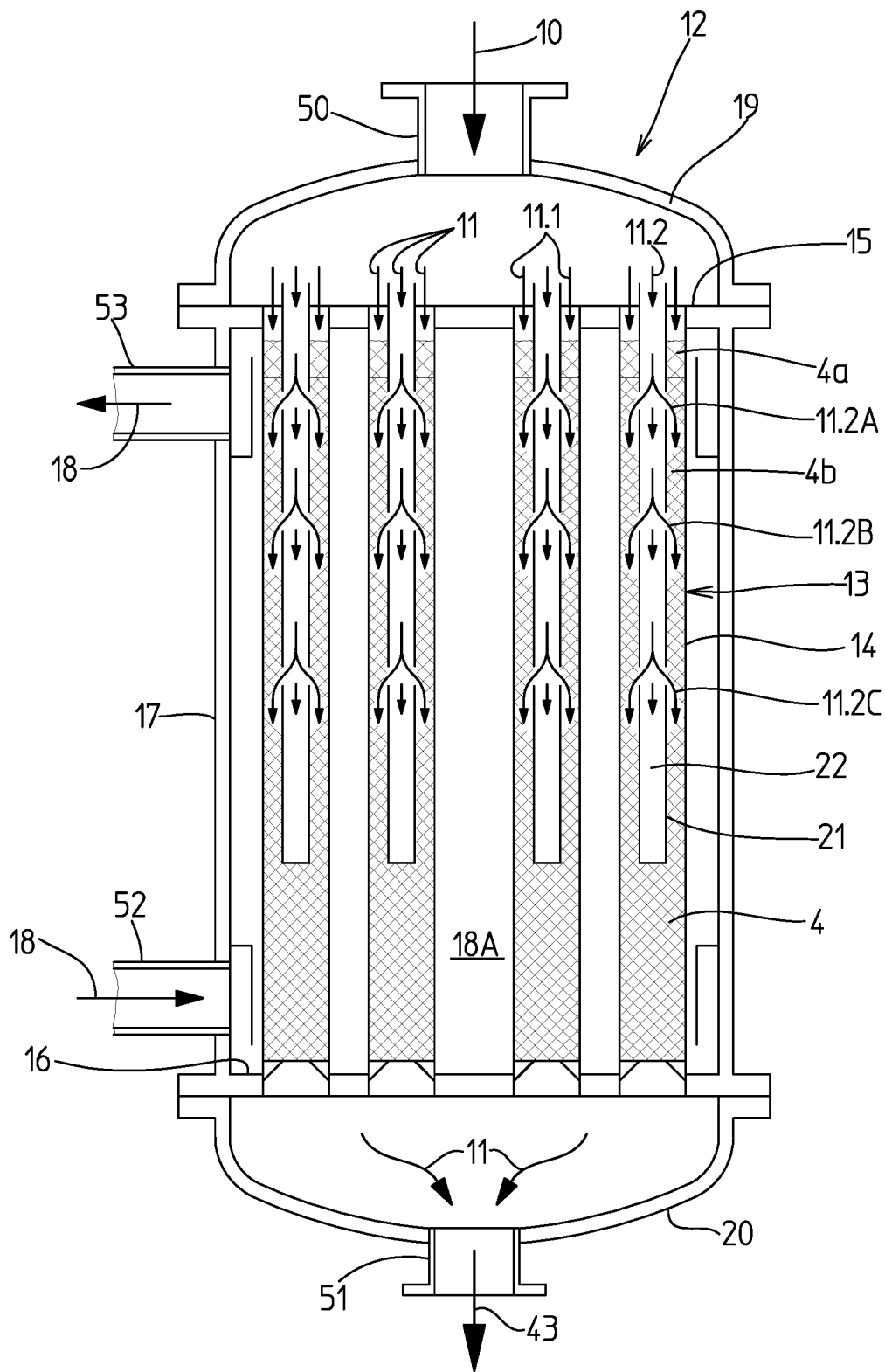
FIG. 1 is a vertical section through a tube bundle reactor.

FIG. 1 shows a boiling water reactor as an exemplary embodiment of a tube bundle reactor according to one aspect of the invention.

The tube bundle reactor 12 comprises a bundle 13 having a plurality of catalyst-filled reaction tubes 14 which extend vertically between an upper tube base 15 and a lower tube base 16 and are enclosed by a cylindrical reactor jacket 17. The two ends of the reaction tubes 14 are welded in a gastight manner to the respective tube base 15, 16. During operation the reaction tubes 14 have a reaction gas 11 flowing through them—in the depicted exemplary embodiment from top to bottom—and are cooled by a heat transfer medium 18. In this case, the two tube bases 15, 16 together with the jacket 17 form a heat transfer medium space 18A into which the heat transfer medium 18 enters through an inlet line 52 in the lower end region of the reactor jacket 17 and from which the heat transfer medium 18 exits through an outlet line 53 in the upper end region of the reactor jacket 17. The upper tube base 15 is spanned by a gas inlet hood 19 with a gas inlet connector 50 and the lower tube base 16 is spanned by a gas outlet hood 20 with a gas outlet connector 51.

Figure 2:
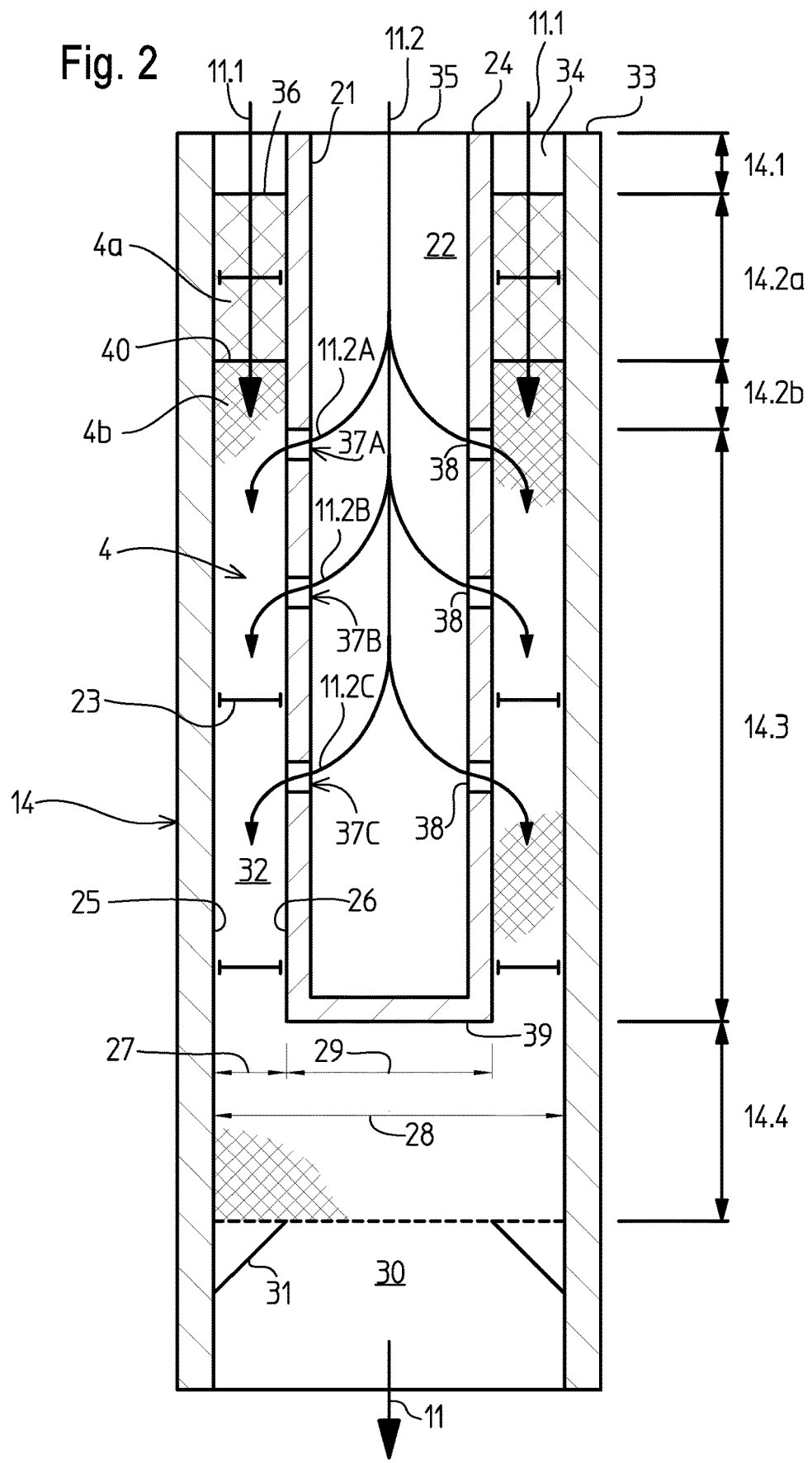
FIG. 2 is in enlarged scale a sectional view through a reaction tube from the tube bundle reactor from FIG. 1.

The reaction tubes 14 are filled with a catalyst charge 4, wherein in each reaction tube 14 a metering tube 21 is arranged coaxially to this, the interior of which is catalyst-free. FIG. 2 shows a catalyst-filled reaction tube 14 with metering tube 21 in detail. The reaction tube 14 and the metering tube 21 are shown not to scale there and in FIG. 1. The length/diameter ratio of reaction tubes 14 and metering tubes 21 is in reality substantially greater.

The metering tube 21 extends by a predefined length into the reaction tube 14 and is fixed by spacers 23 in its central position. The metering tube 21 is fastened in a manner not shown here at its gas-inlet-side end 24 on the reaction tube 14 or also on the neighbouring upper gas-inlet-side tube base 15. An annular gap 27 is formed between the inner wall 25 of the reaction tube 14 and the outer wall 26 of the metering tube 21, the size of the gap being dimensioned so that the square ratio of the internal diameter 28 of the reaction tube 14 to the external diameter 29 of the metering tube 21 lies in a range of 2 to 6.

A catalyst holder 31 on which the catalyst charge 4 rests is arranged in the gas-outlet-side end region 30 of each reaction tube 14. This extends from the catalyst holder 31 as far as the metering tube 21 and then further into the annular space 32 between reaction tube 14 and metering tube 21 up to a predefined distance from the gas-inlet-side end 33 of the reaction tube 14. At the gas-inlet-side reaction tube end 33 a catalyst-free free space 34 is formed as a result. This prevents catalyst material from blowing away since turbulence can form in the reaction gas flow 11 at the gas inlet of the reaction tubes 14. In addition, in a manner not shown here a gas-permeable element, e.g. a perforated sheet or a wire mesh, can be arranged in the lower region of the free space 34 in order to fix the catalyst in its position.

The ratio of the annular gap 27 between the inner wall 25 of the reaction tube 14 and the outer wall 26 of the metering tube 21 to the particle diameter of the catalyst charge 4 lies in the range of 2 to 6.

The gas-inlet-side end 24 of the metering tube 21 forms an inflow opening 35 for the reaction gas 11. At a predefined axial distance from the gas-inlet-side end 36 of the catalyst charge 4, i.e. downstream of the free space 34, a first gas outflow point 37A is arranged and in the depicted example, at further predefined axial distances from this, a second and a third, last gas outflow point 37B, 37C. A gas outflow point is formed by one or more gas outflow openings 38, which are preferably uniformly distributed over the circumference of the metering tube 21. The gas outflow openings 38 of a gas outflow point 37A, 37B, 37C can also be offset with respect to one another in the circumferential direction. The size and number of these gas outlet openings 38 are dimensioned so that a predefined gas flow is established. Furthermore, in a manner not shown here throttle openings can also be arranged inside the metering tube 21.

The metering tube 21 has three functions. It reduces the flow cross-section of the catalyst charge 4 in the reaction tube 14 to the cross-section of the annular space 32 between reaction tube 14 and metering tube 21, with the result that the ensuing reaction heat is reduced. Furthermore, the reaction gas 11 is introduced in an axially stepped manner, with the result that the total reaction heat is divided into several smaller fractions. Finally, transversely to the flow direction of the reaction gas 11, the heat diversion path is shortened to the size of the annular gap 27 between reaction tube 14 and metering tube 21 so that not only less reaction heat is produced but this is also diverted more rapidly.

The catalyst charge 4 is divided into two catalyst layers 4a, 4b. The first catalyst layer 4a in the flow direction of the reaction gas 11 has a lower activity than the adjoining second catalyst layer 4b. Said first catalyst layer 4a begins at the gas-inlet-side end 36 of the catalyst charge 4 in the annular space 32 and ends upstream of the first gas outflow point 37A.

The two catalyst layers 4a, 4b contain the same catalyst material, wherein the first catalyst layer 4a is a mixture containing 5 vol. % to 90 vol. %, preferably 10 vol. % to 40 vol. % of the catalyst material of the second catalyst layer 4b and also inert material. The particle sizes of the catalyst material and the inert material are preferably the same to avoid demixing in particular when filling the reaction tubes 14.

The axial spacing between the gas-inlet-side end 36 of the catalyst charge 4 and the first gas outflow point 37A, the axial spacings between the gas outflow points 37A, 37B, 37C and the axial spacing between the last gas outflow point 37C and the downstream end 39 of the metering tube 21 are predefined so that a heating surface loading due to the released reaction heat between the gas inflow or gas outflow points 35, 37A, 37B, 37C is obtained in the range of 10 kW/m$^2$ to 150 kW/m$^2$, preferably in the range of 20 kW/m$^2$ to 50 kW/m$^2$.

The flow path of the reaction gas 11 through the tube bundle reactor 3 is described hereinafter with reference to FIGS. 1 and 2.

A preheated feed gas 10 enters through the gas inlet connector 50 into the gas inlet hood 19 of the tube bundle reactor 12 and is distributed there. now designated as reaction gas 11, among the reaction tubes 14.

In each reaction tube 14 the reaction gas flow entering there is divided into a first partial flow 11.1 which enters directly into the catalyst charge 4 located in the annular space 32 between metering tube 21 and reaction tube 14, and into a second partial flow 11.2 which enters into the inflow opening 35 of the metering tube 21 and is there guided in the bypass to the catalyst charge 4 until it emerges from the gas outflow points 37A, 37B, 37C as partial flows 11.2A, 11.2B, 11.2C into the catalyst charge 4. The gas-inlet-side end 36 of the catalyst charge 4 thus forms the introduction point for the partial flow 11.1 and the gas outflow points 37A, 37B, 37C form the introduction points for the partial flows 11.2A, 11.2B, 11.2C into the catalyst charge 4.

The first partial flow 11.1 introduced directly into the annular space 32 flows through the free space 34—reaction tube section 14.1—and then enters into the catalyst layer 4a of the catalyst charge 4 in the reaction tube section 14.2.

The reaction tube section 14.2 is divided into a reaction tube section 14.2a which contains the first catalyst layer 4a, with lower activity, and a reaction tube section 14.2b which contains a part of the second catalyst layer 4b.

Preferably the downstream end 40 of the first catalyst layer 4a is located at a predefined distance upstream of the first gas outflow point 37A or the second catalyst layer 4b projects upstream by this distance beyond the first gas outflow point 37A and forms the reaction tube section 14.2b. This reaction tube section 14.2b fulfils the main function of converting the reaction gas 11 as far as almost reaction equilibrium until it reaches the first gas outflow point 37A. A further function lies in providing a safety zone for the case of any settling of the catalyst so that it is ensured that the reaction gas 11 which flows through the first gas outflow point 37A into the catalyst charge 4, flows into an undiluted catalyst layer 4b and can thus react under optimal conditions.

The reaction forms a temperature profile with a hot spot inside the first catalyst layer 4a and is continued towards the downstream end 40 of the first catalyst layer 4a, wherein here a degree of conversion in the range of about 70% to 85% should be understood. The required axial extension of the catalyst layer 4a is determined here with the aid of simulation calculations.

The reaction tube section 14.3 adjoining the reaction tube section 14.2 is a consequence of gas outflow points 37A, 37B, 37C and adjoining reaction sections. Said section begins with the first gas outflow point 37A and ends with the downstream end 39 of the metering tube 21. The partial flows 11.2A, 11.2B, 11.2C of the reaction gas 11 added at the gas outflow points 37A, 37B, 37C react in the respectively following catalyst layer 4b as far as the next gas outflow point 37B, 37C or as far as the downstream end 39 of the metering tube 21. The axial spacings of the gas outflow points 37A, 37B, 37C are dimensioned so that the reaction of the respectively added partial flows 11.2A, 11.2B is continued as far as the beginning of the next gas outflow point 37B, 37C, wherein a degree of conversion of about 70% to 85% is also to be understood here. In this case, the conversion of the reaction sections at the downstream ends thereof increases in the downstream direction from reaction section to reaction section. This increase in conversion is the result of the increasing degree of dilution and the increasingly strong heat removal due to the ever increasing flow rate. Both effects favour the temperature control. At the end of the last reaction section between the last gas outflow point, here 37C, and the downstream end 39 of the metering tube 21, the degree of conversion lies in the range of about 80% to 90%.

The downstream metering tube end 39 is followed by a last reaction tube section 14.4 with the last part of the catalyst layer 4b of the catalyst charge 4 in which a residual conversion takes place as far as reaction equilibrium. On account of the only small amount of reaction heat produced there, the effects of the metering tube 21 are no longer required. As a result of the larger flow cross-section, the residence time of the reaction gas 11 increases with the result that the reaction can be carried out almost as far as reaction equilibrium. At the end of the reaction tube section 14.4, the conversion then lies in the range of 90% to 99%. Furthermore with reference to FIG. 1, the reaction gas 11 flows out from the reaction tubes 14 into the gas outlet hood 20 of the tube bundle reactor 12 and from there out from this through the gas outlet connector 51. now designated as product gas 43.

Figure 3:
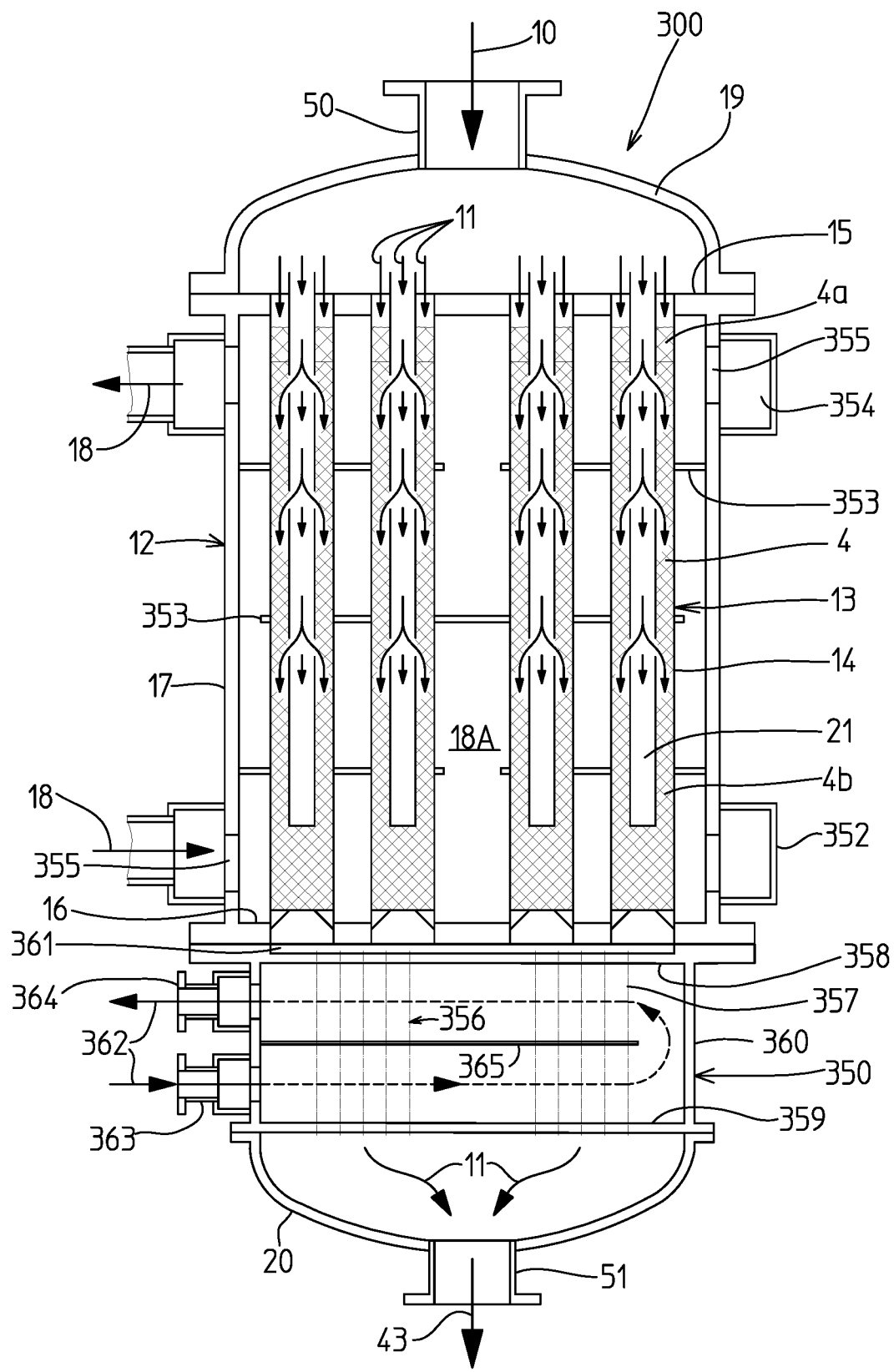
FIG. 3 is a vertical section through a tube bundle reactor.

FIG. 3 shows another exemplary embodiment for a tube bundle reactor according to one aspect of the invention. Here the heat transfer medium is guided by a pump (not shown) in the circuit. Furthermore, a cooler 350 is connected directly to the tube bundle reactor 12 so that both together form a constructive unit 300.

The tube bundle reactor 12, like the tube bundle reactor shown in FIG. 1, comprises a bundle 13 of reaction tubes 14 which are filled with a catalyst charge 4 and in which respectively one metering tube 21 is at least partially embedded in the catalyst charge 4. Flow takes place through the reaction tubes 14 with the metering tubes 21 from top to bottom. Said reaction tubes correspond to the exemplary embodiment shown in FIGS. 1 and 2, i.e. the catalyst charge 4 is divided into two catalyst layers 4a and 4b as described there.

Likewise the upper gas-inlet-side ends of the reaction tubes 14 are fastened in a gastight manner in an upper tube base 15 which is spanned by an upper reaction hood or gas inlet hood 19 with a gas inlet connector 50.

The lower gas-inlet-side ends of the reaction tubes 14 are fastened in a gastight manner in a lower tube base 16 on which the cooler 350 is fastened on the side facing away from the reaction tubes 14.

The reaction tubes 14 are here also enclosed by a cylindrical rector jacket 17 which together with the upper and lower tube bases 15, 16 forms a heat transfer medium space 18A.

In the heat transfer medium space 18A a heat transfer medium 18 flows around the reaction tubes 14, which heat transfer medium 18A is supplied to the heat transfer medium space 18A from a lower annular channel 352 and in the heat transfer medium space 18A is guided through the tube bundle 13 by disk-shaped and annular deflecting plates 353 in a meander shape in the radial direction in each case from outside to inside and conversely and from bottom to top, i.e. transversely to the reaction tubes 14 and in counterflow to the reaction gas 11 and is led off from the heat transfer medium space 18A again from an upper annular channel 354. The reactor channels 352, 354 enclose the reactor jacket 17 on its outer side and are in flow communication with the heat transfer medium space 18A through jacket openings 355. The heat transfer medium 18 is guided in the circuit via a heat exchanger and a heat transfer medium pump, which are both not shown here. Preferably the heat transfer medium 18 is a generally known liquid salt but other heat transfer media can also be used such as, for example, heat transfer medium oil or ionic liquids.

The cooler 350 comprises a bundle 356 of cooling tubes 357, the number of which can be smaller than the number of the reaction tubes 14. The cooling tubes 357 extend from an upper cooler tube base 358 vertically to a lower cooler tube base 359 and are enclosed by a cylindrical cooler jacket 360. The ends of the cooling tubes 357 are welded to the respective cooler tube base 358, 359 in a gastight manner. The cooling tubes 357 are catalyst-free and reaction gas 11 flows through them from top to bottom.

Located between the lower tube base 16 of the tube bundle reactor 12 and the upper cooler tube base 358 is a gas transfer space 361 into which the reaction gas 11 emerges from the reaction tubes 14 and from which it enters into the cooling tubes 357.

The cooling tube bundle 356 has a heat transfer medium 362 flowing through it transversely in a heat transfer medium circuit, which is independent of the heat transfer medium circuit of the tube bundle reactor 12. The heat transfer medium flow enters into the cooler 350 through an inlet connector 363 arranged in the lower end region of the cooler 350 and exits from this again through an outlet connector 364 arranged in the upper end region of the cooler 350. At half height of the cooler 350 a deflecting plate 365 is arranged between the inlet and the outlet connectors 363, 364, which extends horizontally through the entire cooling tube bundle 356 so that the heat transfer medium flow coming from the inlet connector 363 and after its deflection towards the outlet connector 364 is guided transversely through the entire cooling tube bundle 356.

The lower cooler tube base 359 is spanned on its side facing away from the cooling tubes 357 by a lower reactor hood or a gas outlet hood 20 with a gas outlet connector 51.

From the cooling tubes 356 the reaction gas 11 enters into the gas outlet hood 20 and is led out from the cooler through the gas outlet connector 51, now designated as product gas 43.

Figure 4:
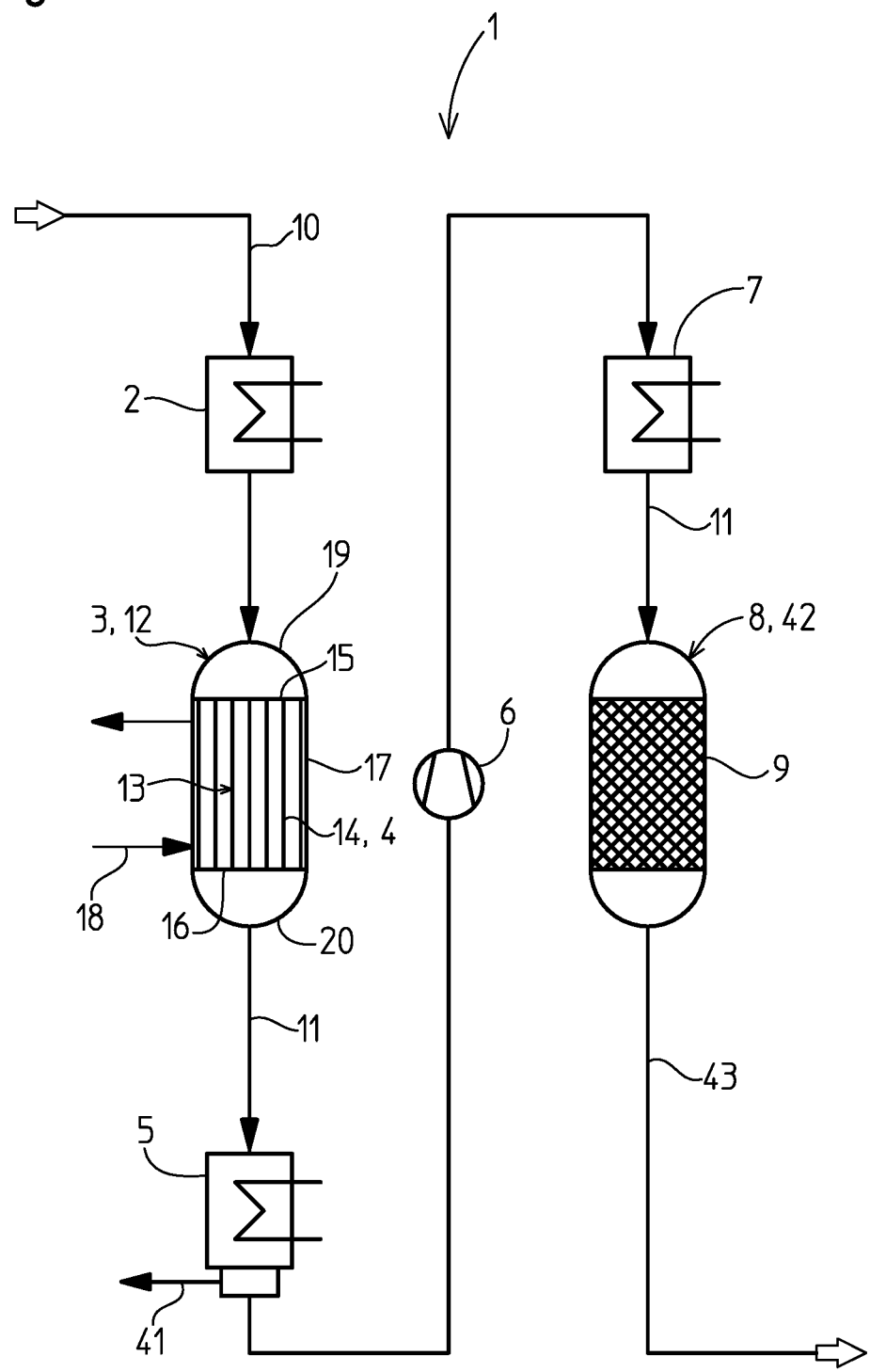
FIG. 4 is a schematic diagram of a reactor system.

The exemplary embodiment of a reactor system 1 according to one aspect of the invention 10 shown in FIG. 4 comprises a preheater 2, a tube bundle reactor according to the invention (e.g. the exemplary embodiments shown in FIG. 1 or 3) as a first reactor stage 3 with a first catalyst charge 4, a condenser 5, a compressor 6, a heating zone 7 and a second reactor stage 8 with a second catalyst charge 9 which are all arranged consecutively in the flow direction of a feed gas 10 or reaction gas 11 flowing through the reactor system 1.

In the preheater 2 the feed gas 10 is heated before its entry into the tube bundle reactor 12 to at least the so-called start-up temperature of the catalyst of the catalyst charge 4. This is the required temperature so that a catalytic conversion takes place. Preferably the feed gas 10 is set to a temperature which is 5 K to 30 K higher than the start-up temperature. A heating in the 20 tube bundle reactor 12 directly before the catalyst charge 4 is also possible. An installation part is saved as a result.

The flow path of the reaction gas through the tube bundle reactor of the first reactor stage has already been described with reference to FIGS. 1 to 3.

In the condenser 5 the reaction gas 11 emerging from the first reactor stage is cooled to a temperature below the dew point of at least one portion of the components of the reaction gas 11 and a portion of the condensed components 41 is led off. In the case of a methanation, the water formed during the reactions in the tube bundle reactor 12 is partially condensed out and led off in lines.

The reactions in the first reactor stage 3 and the temperature decrease in the condenser 5 result in a decrease in volume. In order to produce optimal reaction conditions for maximizing the conversion in the second reactor stage 8, the pressure is then increased in the compressor 6.

In the heating zone 7 the compressed reaction gas 11 is heated to at least the start-up temperature of the second catalyst charge 9 of the second reactor stage 8. In the depicted exemplary embodiment, the second reactor stage 8 is an adiabatic reactor 42. In the adiabatic reactor 42 the conversion of the reaction gas 11 is completed since a high conversion is achieved at relatively low temperature. In the case of a methanation the degree of conversion lies in the range of 98.0% to 99.6%. Following the second reactor stage 8 the water produced in the process is usually almost completely condensed out. The product gas 43 now consists largely of methane $CH_4$ having a methane concentration according to a predefined feed-in specification.

Figure 5:
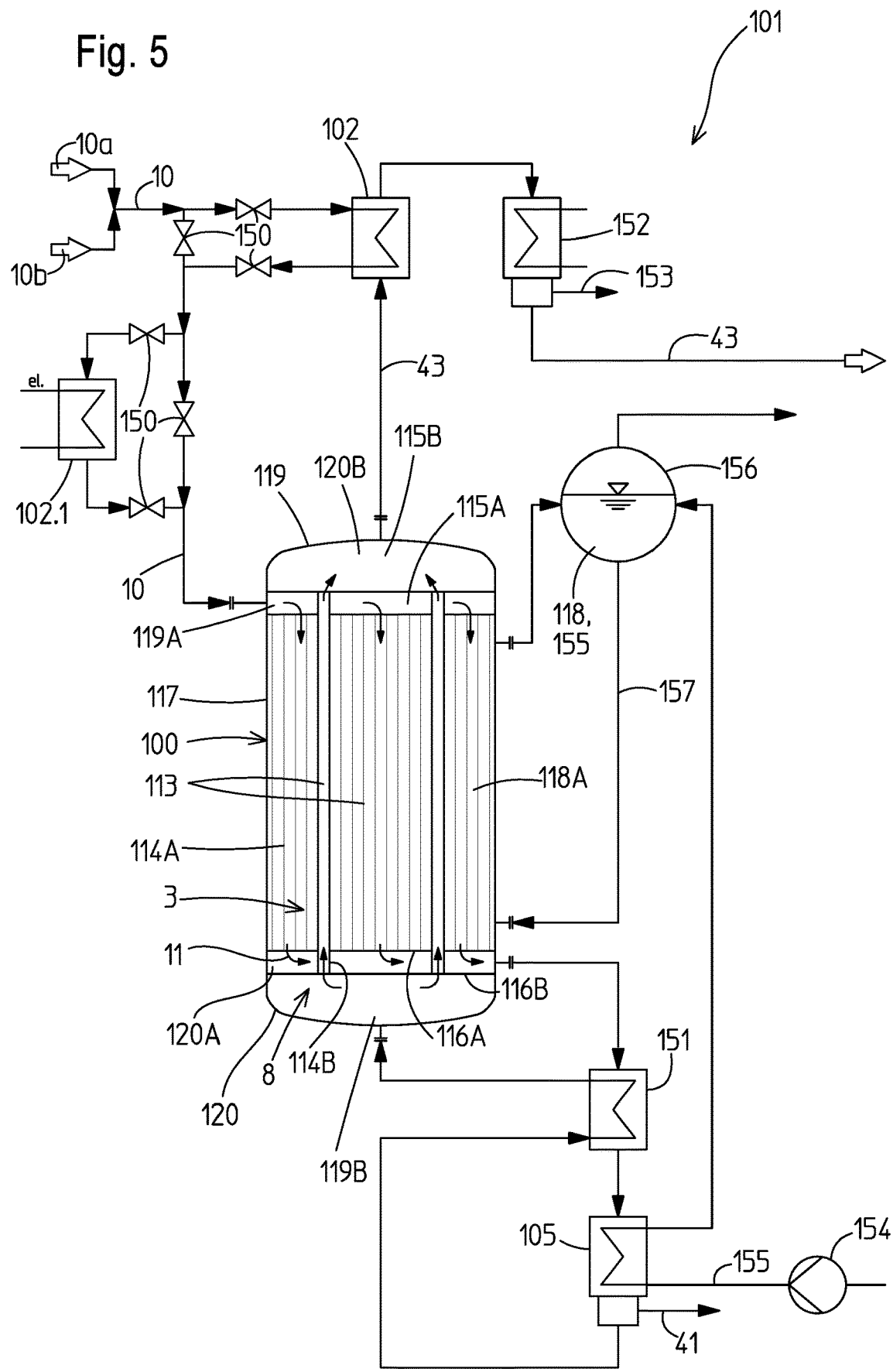
FIG. 5 is a schematic diagram of a reactor system with first and second reactor in the same reactor housing.

In the exemplary embodiment of a reactor system 101 according to the invention shown in FIG. 5, the first and the second reactor stage 3, 8 are configured as a constructive unit in the form of a so-called combi-reactor 100.

The combi-reactor 100 in this exemplary embodiment comprises reaction tubes 114A for the first reactor stage 3 and also reaction tubes 114B for the second reactor stage 8 which are combined in a single tube bundle 113 and distributed there in a mixed manner. The tube bundle 113 is enclosed by a reactor jacket 117 so that the reaction tubes 114A, 114B of the first and the second reactor stage 3, 8 are located in a common heat transfer medium space 118A in which they are cooled by a heat transfer medium 118. Furthermore, the reaction tubes 114A, 114B both of the first and also of the second reactor stage 3, 8 are filled with catalyst material and have reaction gas 11 flowing through, wherein the reaction tubes 114A of the first reactor stage 3 are in flow communication with a different gas distributor space and gas collecting space from the reaction tubes 114B of the second reactor stage 8.

The reactor tubes 114A of the first reactor stage 3 are filled with the first catalyst charge 4 which, as described above, is divided at least into one catalyst layer 4a and one catalyst layer 4b and through which flow takes place from top to bottom. They are fastened in a gastight manner at the ends thereof to a first upper and a first lower tube base 115A, 116A. A metering tube 21 is arranged coaxially in each reaction tube 114A of the first reactor stage 3, which metering tube is embedded at least partially in the first catalyst charge 4. The metering tubes 21 and this first catalyst charge 4 can be configured, for example, as shown in FIG. 2.

The reaction tubes 114B of the second reactor stage 8 are filled with the second catalyst charge 9 and flow takes place through said tubes from bottom to top. They are fastened at the ends thereof in a gastight manner to a second tube base 115B which is arranged at a distance above the first upper tube base 115A and in a second lower tube base 116B which is arranged below the first lower tube base 116A. The reaction tubes 114B of the second reactor stage 8 are exclusively filled with the second catalyst charge 9 and contain no metering tubes.

The second upper tube base 115B is spanned by an upper reactor hood 119 and the second tube base 116B is spanned by a lower reactor hood 120.

The intermediate space between the first upper and the second upper tube base 115A, 115B forms the (first) gas inlet space 119A and the intermediate space between the first lower and the second lower tube base 116A, 116B forms the (first) gas collecting space 120A for the reaction tubes 114A of the first reactor stage 3.

The lower reactor hood 120 forms the second gas inlet space 119B and the upper reactor hood 119 forms the second gas collecting space 120B for the reaction tubes 114B of the second reactor stage 8.

The exemplary embodiment of a reactor system 101 shown in FIG. 5 is described as follows:

A gas flow having a first feed gas component 10a and a gas flow having a second feed gas component 10b, in the case of a methanation, for example, a gas flow of $CO_2$ and a gas flow of $H_2$, are combined in a mixer not shown here to form a feed gas 10. This is heated before entry into the first reactor stage 3 in continuous stationary operation in the counterflow in a preheater 102 by the product gas 43 coming from the second reactor stage 8 to the start-up temperature of the first catalyst charge 4. When starting up the reactor system 101 however, there is still no hot product gas 43. The feed gas 10 is therefore heated during the start-up process by a preferably electrically operated start-up preheater 102.1. The operation of this start-up preheater 102.1 is possible in any arbitrary manner, for example, with steam if a steam network is present. The feed gas flow 10 is deflected by appropriate opening or closing of shutoff valves 150 in the pipeline.

The preheated feed gas 10 then flows into the first gas distributor space 119A of the first reactor stage 3 of the combi-reactor 100 and from there into the reaction tubes 114A with the metering tubes 21. After emerging from these reaction tubes 114A, the reaction gas 11 is led into the first gas collecting space 120A.

From there it is guided into a heat transfer medium 151 where it delivers a first portion of its heat.

Then the water 41 contained in the reaction gas 11, in the case of a methanation, is partially condensed in a condenser 105 and led off so that the reaction gas 11 only contains a water content of about 20 vol. %. The cooled reaction gas 11 is then heated again in the heat transfer medium 151 before it is guided into the second gas distributor space 119B of the second reactor stage 8 of the combi-reactor 100. From there the reaction gas 11 flows into the reaction tubes 114B of the second reactor stage 8 where the residual conversion takes place as far as the desired product composition. The reaction gas 11 then enters from these reaction tubes 114B into the second gas collecting space 120B in the upper reactor hood 119, from where it is guided out from the combi-reactor 100 as product gas 43.

In the adjoining above-mentioned preheater 102, the product gas 43 heats the feed gas 10 entering into the first reactor stage 3 and is then guided into a second condenser 152 where the water 153 still formed in the second reactor stage 8 condenses out and it led off. The dry product gas 43 is then transferred to the gas feed-in unit.

The combi-reactor 100 shown is a boiling water reactor. The operating pressure is 55 bara so that an operating temperature of 270° C. is obtained. In order that the heat management is as efficient as possible, feed water is used at least partially as cooling medium for the condensers. In the exemplary embodiment shown the feed water 155 supplied by means of a pump 154 is used as coolant in the condenser 105 between first and second reactor stage 3,8 before it is supplied to the steam drum 156 of the coolant circuit 157 of the boiling water reactor 100.

The reactor system 101 is further equipped with a measurement, control and regulation system not shown here such as is customary for plants of this type. In particular, the composition of the reaction gas 11 between first and second reactor stage 3,8 is analyzed. Here it is checked whether the conversion of the first reactor stage 3 is sufficiently high so that the residual conversion in the second reactor stage 8 does not result in inadmissibly high temperatures.

Temperature measurement points are furthermore expedient in all process flows and in the second reactor stage 8. The process flows here comprise the feed gas components 10a, 10b before and after mixing, the reaction gas 11, the heat transfer medium 118, condensed-out water 41, 43, feed water 155 for the boiling water circuit 157 and possible other auxiliary flows.

Figure 6:
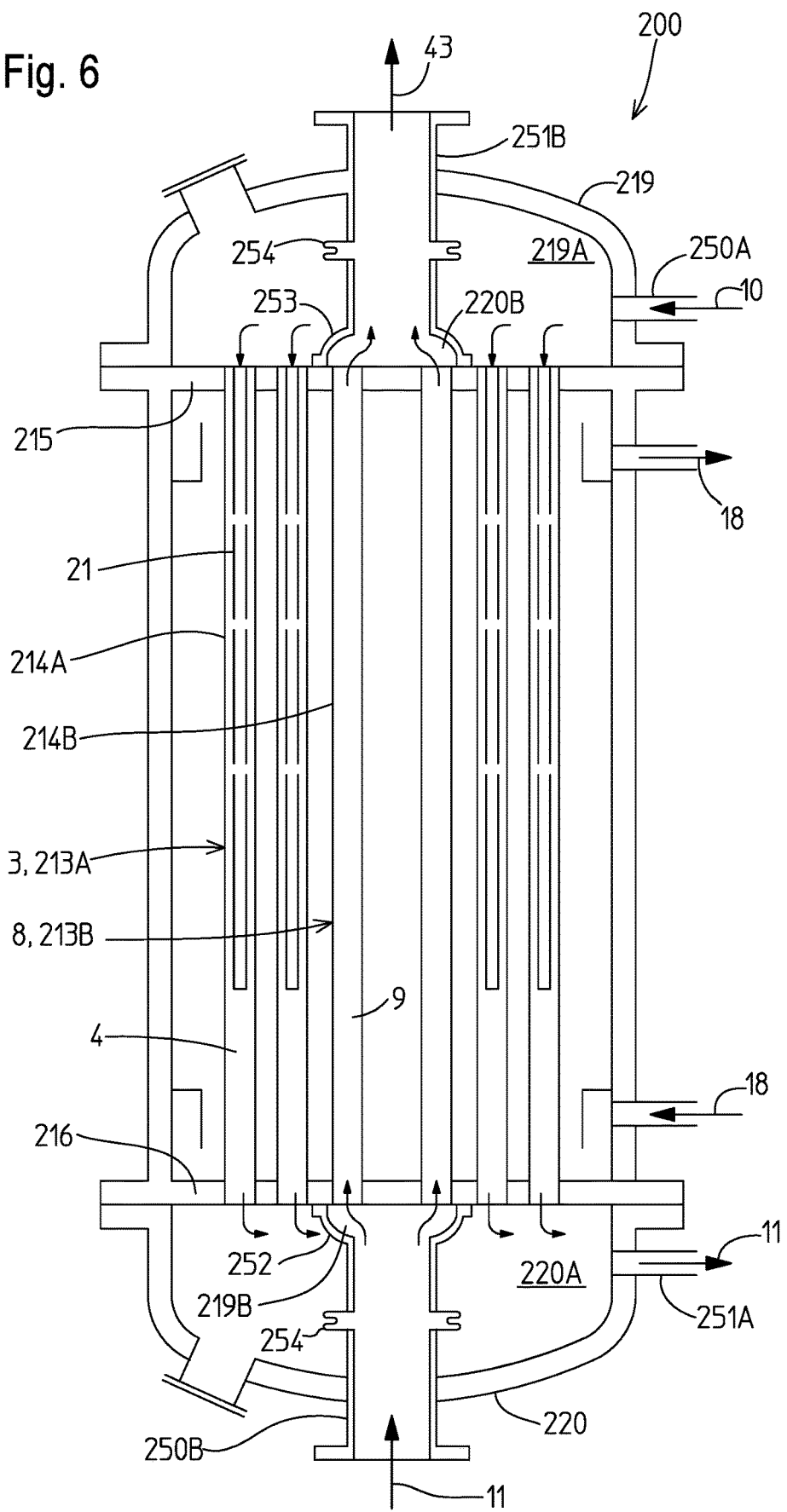
FIG. 6 is a vertical section through a reactor housing of a tube bundle reactor with first and second reactor stage in the same reactor housing.

FIG. 6 shows a variant 200 of the combi-reactor 100 shown in FIG. 5. The difference lies in the fact that the reaction tubes 214A, 214B of the first and second reactor stage 3, 8 are not distributed uniformly over the reactor cross-section but are arranged in respectively their own regions. Thus, the reaction tubes 214A of the first reactor stage 3 are arranged in an annular tube bundle 213A which encloses a central tube bundle 213B with the reaction tubes 214B of the second reactor stage 8.

As in the exemplary embodiment according to FIG. 5, the reaction tubes 214A of the first reactor stage 3 each contain a coaxially arranged metering tube 21 which is at least partially embedded in the first catalyst charge 4. As described above, the first catalyst charge 4 is divided into a catalyst layer 4a and a catalyst layer 4b. The reaction tubes 214B of the second reactor stage 8 are exclusively filled with the second catalyst charge 9; they do not contain metering tubes.

The upper reactor hood 219 forms the first gas distributor space 219A of the first reactor stage 3 and has a gas inlet connector 250A for the feed gas 10. The lower reactor hood 220 forms the first gas collecting space 220A of the first reactor stage 3 and has a gas outlet connector 251A for the reaction gas 11.

The second gas distributor space 219B of the second reactor stage 8 is formed by a distributor hood 252 which is arranged inside the lower reactor hood 220, i.e. inside the first gas collecting space 220A and is connected to a second gas inlet connector 250B which extends through the lower reactor hood 220 and out from this. The second gas collecting space 220B is formed by a collecting hood 253 which is arranged inside the upper reactor hood 219, i.e. inside the first gas distributor space 219A and is connected to a second gas outlet connector 251B which extends through the upper reactor hood 219 and out from this.

The distributor hood 252 is fastened to the side of the lower tube base 216 facing the lower reactor hood 220. The collecting hood 253 is fastened on the side of the upper tube base 215 facing the upper reactor hood 219.

In order to compensate for manufacturing tolerances and temperature expansions, the second gas inlet connector 250B and the second gas outlet connector 251B each have an expansion component 254.

The operating mode is as follows:

The feed gas 10 is introduced into the first gas distributor space 219A and from there enters into the reaction tubes 214A of the first reactor stage 3.

From the reaction tubes 214A of the first reactor stage 3, the reaction gas 11 enters into the first gas collecting space 220A and is led out from the combi-reactor 200 by the first gas outlet connector 251A.

The reaction gas 11 is then cooled so far in a condenser not shown here that the water contained in the reaction gas 11, in the case of a methanation, is condensed and a portion of the water is led off. The reaction gas 11 is then again heated in a heating zone also not shown here to the start-up temperature of the second catalyst charge 9 of the second reaction stage 8.

The heated reaction gas 11 then enters into the combi-reactor again through the second gas inlet connector 250B and is then supplied to the second gas distributor space 219B (the distributor hood 252).

From the distributor hood 252 the reaction gas 11 enters into the reaction tubes 214B of the second reactor stage 8.

From these reaction tubes 214B the reaction gas 11 enters into the second gas collecting space 220B, the collecting hood 253, and is led out from the combi-reactor 200 as product gas 43 by the second gas outlet connector 251B.

The gas is transferred to the gas feed-in unit and optionally previously to another condenser for condensing out the water still contained in the reaction gas 11 after the second reactor stage 8 or in the now product gas 43.

As a result of the exemplary embodiments of the second reactor stage 8 shown in FIG. 5 and FIG. 6 as a tube bundle reactor integrated in the combi-reactor 100, 200, it is possible to control the entire reaction even more effectively and optimize the size of the entire reactor system 101. The particular advantage of these reactor systems 101 lies in that any overheating in the second reactor stage 8 can be eliminated by the cooling and the conversion can be held at a stable and high level, wherein at the same time a compact design is achieved.

Figure 7:
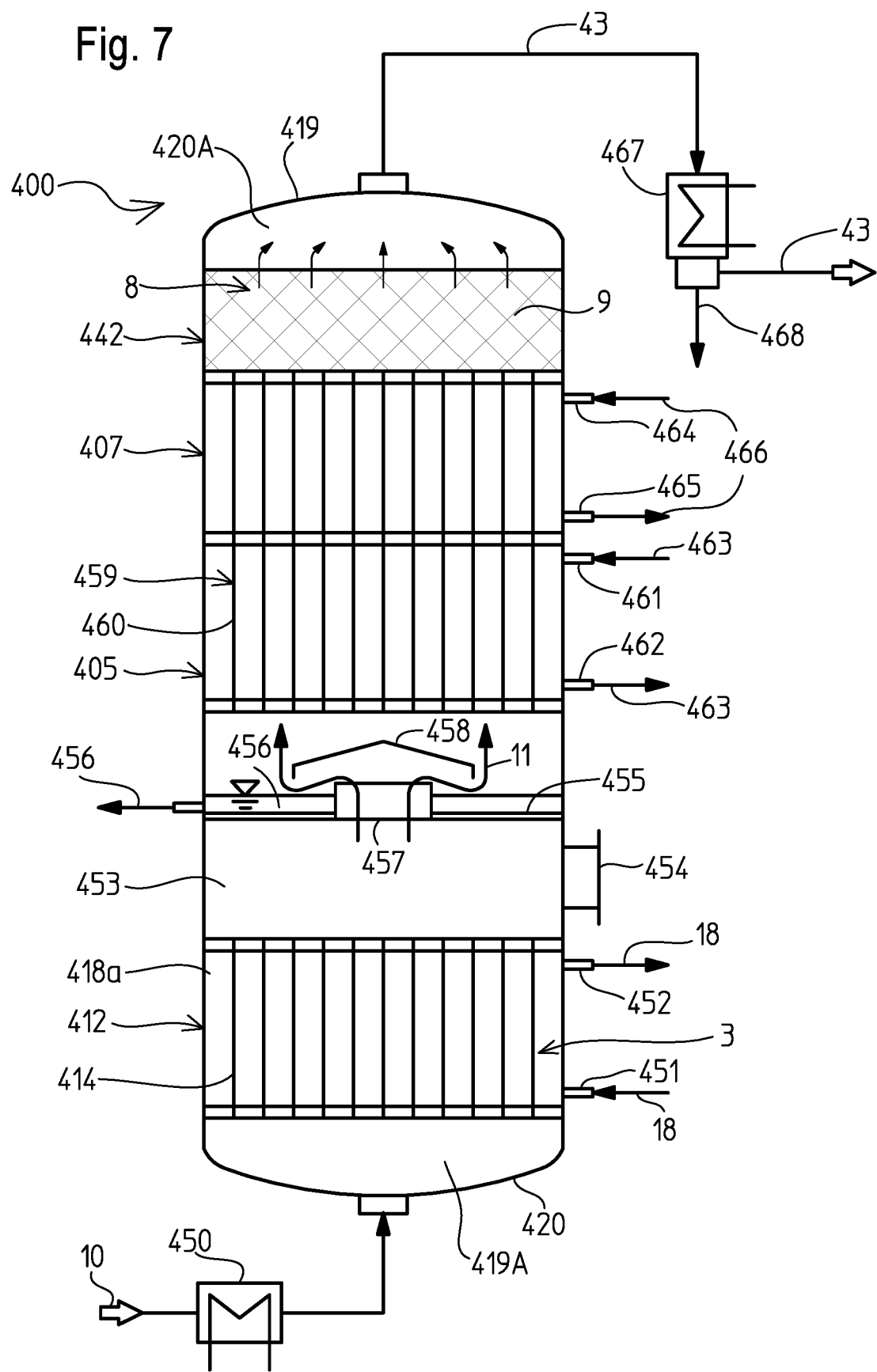
FIG. 7 is a vertical section through a reactor housing of a tube bundle reactor with first and second reactor stage as well as condenser and heating zone in the same reactor housing.

FIG. 7 shows as an exemplary embodiment a combi-reactor 400 in which all the components of the rector system are accommodated in a housing. The reaction gas 11 flows through this combi-reactor 400 from bottom to top. In detail, the combi-reactor 400 contains the following components:

A lower reactor hood 420 forms a gas distributor space 419A into which the feed gas 10 preheated in a preheater 450 enters.

The gas distributor space 419A adjoins the tube bundle reactor 412 as first reactor stage 3. The reaction tubes 414 of the tube bundle reactor 412 contain the first catalyst charge 4 in which metering tubes 21 are at least partially embedded, similarly to that shown in FIG. 2. However, the metering tubes 21 are turned through 180° with respect to FIG. 2 so that their gas inlet opening is in each case in flow communication with the gas distributor space 419A. The sequence of the catalyst layers 4a, 4b in the flow direction of the reaction gas corresponds to that in FIG. 2. That is, in the tube bundle reactor 412 the catalyst layer 4a lies below the catalyst layer 4b so that the reaction gas partial flow 11.1 entering flow below directly into the annular space between metering tube and reaction tube again enters firstly into the catalyst layer 4a of lower activity.

Via a heat transfer medium inlet connector 451 and a heat transfer medium outlet connector 452, a heat transfer medium 18 is guided in a heat transfer medium circuit here in direct flow with the reaction gas 11 through the heat transfer medium space 418A. The heat transfer medium 18 can, for example, be liquid or boiling water or pressurized water.

Above the tube bundle reactor 412 of the first reactor stage 3, a working chamber 453 is provided for a fitter. The working chamber 453 is accessible through a manhole 454 and is used for filling the reaction tubes 414 with catalyst material during the initial filling or for replacing the catalyst material and for other work such as, for example, the installation of thermometers.

Located above this working chamber 453 is a device 455 for collecting condensed components 456 of the reaction gas 11, in the case of a methanation therefore water, and for leading off the condensed components 456. The said device 455 is penetrated by at least one roofed-over opening 457 for reaction gas 11 so that the reaction gas 11 can flow from the first reactor stage 3 in the combi-reactor 400 further upwards to the following components. The roof 458 prevents the condensed components from being able to pass back into the working chamber 453 or into the first reactor stage 3.

Above this region there follows a condenser 405 with a bundle 459 of catalyst-free cooling tubes 460 through which the reaction gas 11 flows, which is cooled so far that a portion of the components, for example water, condenses. The condensed components 456 flow into the cooling tubes 460 downwards into the collecting and removal region 455, 456. The condenser 405 has an inlet connector 461 and an outlet connector 462 for the coolant 463 which is here guided in counterflow to the reaction gas flow through the condenser 405. For example, water can be used as coolant 463.

The condenser 405 is followed by a heating zone 407 in which the reaction gas 11 emerging from the condenser 405 is heated to the reaction temperature of the second catalyst charge 9 in the second reactor stage 8. In the exemplary embodiment shown the tubes 460 extend continuously through the condenser 405 and the heating zone 407 and are free of catalyst material. Via an inlet connector 464 and an outlet connector 465 heat transfer medium 466 is here guided in counterflow to the reaction gas flow through the heating zone 407. The heat transfer medium 466 can be, for example, liquid salt or boiling water or pressurized water as in the first reactor stage 3.

From the heating zone 407 the reaction gas 11 enters into the second reactor stage 8 which in the depicted exemplary embodiment is an adiabatic reactor 442. This contains the second catalyst charge 9 in which the residual conversion of the reaction gas 11 takes place.

From the second reactor stage 8 the reaction gas 11 enters into the upper reactor hood 419 which forms the gas collecting space 420A from which the finished reaction gas emerges as product gas 43. If the product gas 43—for example, in the case of a methanation—is still too damp, it can be fed to a further condenser 467 in which the residual moisture 468 is condensed out.

The exemplary embodiments do not constitute any restriction in the embodiments of the invention. In particular, individual features of a specific exemplary embodiment can be used in adapted design advantageously in other designs. Thus, for example, it is also possible that flow takes place from bottom to top in the tube bundle reactor in FIG. 1, as shown in FIG. 7.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A tube bundle reactor, comprising:
a bundle of reaction tubes that are filled with a catalyst charge and through which a reaction gas flows during operation and which are cooled by a heat transfer medium;
a metering tube is embedded at least partially in the catalyst charge in each reaction tube and arranged coaxially thereto,
wherein the metering tube extends from a gas-inlet-side end of the catalyst charge a predefined length into the catalyst charge,
wherein an interior of the metering tube is catalyst-free,
wherein the metering tube has at least one gas inflow point outside the catalyst charge, and
wherein the metering tube has at least one first gas outflow point in a region of the catalyst charge,
wherein the at least one first gas outflow point in a flow direction of the reaction gas is arranged at a predefined distance from the gas-inlet-side end of the catalyst charge so that a partial flow of the reaction gas flowing into each reaction tube flows in a bypass to the catalyst charge there,
wherein:
a first catalyst charge of the catalyst charge has at least two catalyst layers of different activity,
the at least two catalyst layers contain a same catalyst material,
a first catalyst layer of the at least two catalyst layers in the flow direction of the reaction gas contains 5 vol. % to 90 vol. % of the catalyst material of a directly adjacent at least one second catalyst layer of the at least two catalyst layers, and
a first gas outflow point in the flow direction of the reaction gas of the at least one first gas outflow point opens into the at least one second catalyst layer,
wherein the catalyst material is a methanation catalyst.

2. The tube bundle reactor according to claim 1,
wherein the first catalyst layer comprises particles,
wherein in each reaction tube a ratio of an annular gap between an inner wall of the reaction tube and an outer wall of the metering tube to a particle diameter of the first catalyst layer lies in a range of 2 to 6.

3. The tube bundle reactor according to claim 1, wherein:
an axial spacing between the at least one gas inflow point and the first gas outflow point in the flow direction of the reaction gas,
an axial spacing between the respective gas outflow points, and
an axial spacing between a last gas outflow point and an end of the metering tube and a number thereof
are each selected so that a heating surface loading due to reaction heat released between the gas inflow and outflow points is in a range of at least one of 10 kW/m² to 150 kW/m² and 20 kW/m² to 50 kW/m².

4. The tube bundle reactor according to claim 1, wherein a square ratio of an internal diameter of each reaction tube to an external diameter of the metering tube lies in a range of 2 to 6.

5. A reactor system, comprising:
a first reactor stage;
a condenser;
a heating zone; and
a second reactor stage which are all arranged consecutively in a flow direction of a reaction gas flowing through the reactor system, wherein
the first reactor stage is a tube bundle reactor comprising:
a bundle of reaction tubes that are filled with a catalyst charge and through which the reaction gas flows during operation and which are cooled by a heat transfer medium;
a metering tube is embedded at least partially in the catalyst charge in each reaction tube and arranged coaxially thereto,
an interior of the metering tube is catalyst-free and extends from a gas-inlet-side end of the catalyst charge into the catalyst charge a predefined length, and the metering tube has at least one gas inflow point outside the catalyst charge and at least one gas outflow point in a region of the catalyst charge,
wherein a first gas outflow point, of the at least one gas outflow point, in a flow direction of the reaction gas is arranged at a predefined distance from the gas-inlet-side end of the catalyst charge so that a partial flow of the reaction gas flowing into each reaction tube flows in a bypass to the catalyst charge there,
wherein:
a first catalyst charge of the catalyst charge has at least two catalyst layers of different activity,
the at least two catalyst layers contain a same catalyst material,
a first catalyst layer of the at least two catalyst layers in the flow direction of the reaction gas contains 5 vol. % to 90 vol. % of the catalyst material of a directly adjacent at least one second catalyst layer of the at least two catalyst layers, and
the first gas outflow point in the flow direction of the reaction gas opens into the at least one second catalyst layer,
wherein the reaction gas flowing into the reactor system is conveyed through the catalyst charge,
wherein the condenser is configured to cool the reaction gas flowing out of the tube bundle reactor to a temperature below a dew point of at least a portion of components of the reaction gas and to divert the at least the portion of condensed components,
wherein the heating zone is configured to heat the reaction gas from which a portion of the condensed components has been removed in the condenser; and
wherein the second reactor stage is a reactor with a second catalyst charge, through which the reaction gas flowing out from the heating zone is conveyed,
wherein the catalyst material is a methanation catalyst.

6. The reactor system according to claim 5, wherein at least two components of the first reactor stage, the condenser, the heating zone, and the second reactor stage form a constructive unit.

7. The reactor system according to claim 5, wherein the second reactor stage is a cooled reactor whose average heat transfer medium temperature is 0 K to 30 K lower than a heat transfer temperature of the reactor of the first reactor stage.

8. The reactor system according to claim 7, wherein the second reactor stage is a tube bundle reactor having a bundle of reaction tubes filled with the second catalyst charge and through which a reaction gas flows during operation and which are cooled by a heat transfer medium.

9. The reactor system according to claim 8, wherein the reaction tubes of the two reactors of the first and second reactor stages are located in a common heat transfer medium space.

10. The reactor system according to claim 5, wherein the first catalyst layer of the at least two catalyst layers in the flow direction of the reaction gas contains 10 vol. % to 40 vol. % of the catalyst material of the directly adjacent at least one second catalyst layer of the at least two catalyst layers.

11. The reactor system according to claim 5, wherein the methanation catalyst contains one or more VIII side group elements.

12. The reactor system according to claim 5, wherein the methanation catalyst contains nickel.

* * * * *